US006602282B1

United States Patent
Yan (10) Patent No.: US 6,602,282 B1
(45) Date of Patent: Aug. 5, 2003

(54) FLEXIBLE STENT STRUCTURE (75) Inventor: John Yan, Los Gatos, CA (US)

(73) Assignee: Avantec Vascular Corporation, San Jose, CA (US)

( * ) Notice: Subject to any disclaimer, the term of this patent is extended or adjusted under 35 U.S.C. 154(b) by 0 days.

(21) Appl. No.: 09/565,560

(22) Filed: May 4, 2000

(51) Int. Cl.[7] .................................. A61F 2/06
(52) U.S. Cl. ................................. 623/1.15
(58) Field of Search ................. 623/1.11–1.16, 623/1, 1.17–1.23; 606/198, 194, 195

(56) References Cited

U.S. PATENT DOCUMENTS

| | | | |
|---|---|---|---|
| 4,776,337 A | 10/1988 | Palmaz | 128/343 |
| 5,102,417 A | 4/1992 | Palmaz | 606/96 |
| 5,697,971 A * | 12/1997 | Fischell et al. | 623/1.15 |
| 5,755,781 A * | 5/1998 | Jayaraman | 623/1.15 |
| 5,807,404 A * | 9/1998 | Richter | 623/1.16 |
| 5,911,754 A * | 6/1999 | Kanesaka et al. | 623/1.15 |
| 5,922,020 A | 7/1999 | Klein et al. | 623/1 |
| 6,013,854 A | 1/2000 | Moriuchi | 623/11 |
| 6,015,429 A | 1/2000 | Lau et al. | 623/1 |
| 6,017,362 A | 1/2000 | Lau | 623/1 |
| 6,017,365 A | 1/2000 | Von Oepen | 623/1 |
| 6,042,597 A * | 3/2000 | Kveen et al. | 623/1.15 |
| 6,068,656 A * | 5/2000 | Von Oepen | 623/1.15 |
| 6,083,259 A * | 7/2000 | Frantzen | 623/1.15 |
| 6,106,548 A * | 8/2000 | Roubin et al. | 623/1.15 |
| 6,217,608 B1 * | 4/2001 | Penn et al. | 623/1.15 |
| 6,235,053 B1 * | 5/2001 | Jang | 623/1.15 |
| 6,342,067 B1 * | 1/2002 | Mathis et al. | 623/1.15 |

FOREIGN PATENT DOCUMENTS

| | | | |
|---|---|---|---|
| EP | 0 662 307 A1 | 7/1995 | A61F/2/06 |
| EP | 0 662 307 B1 | 5/1998 | A61F/2/06 |
| WO | WO 9917680 | 4/1999 | A61F/2/04 |
| WO | WO 00/03662 | 1/2000 | A61F/2/06 |

* cited by examiner

*Primary Examiner*—Michael J. Milano
*Assistant Examiner*—(Jackie) Tan-Uyen T. Ho
(74) *Attorney, Agent, or Firm*—Townsend and Townsend and Crew LLP (57) ABSTRACT

Luminal prostheses comprise adjacent expansible segments, typically serpentine ring segments joined by sigmoidal links. By properly orienting the sigmoidal links and aligning hinge regions on adjacent serpentine rings, enhanced opening characteristics can be obtained. Additionally, by varying the mechanical characteristics of adjacent serpentine rings, program expansion of the luminal prostheses over their lengths may be obtained. The disclosed prostheses also have controllable opening characteristics and can be crimped to small diameters.

26 Claims, 10 Drawing Sheets

FLEXIBLE STENT STRUCTURE

BACKGROUND OF THE INVENTION

1. Field of the Invention

The present invention relates generally to medical devices and methods. More particularly, the present invention relates to radially expansible luminal prostheses, such as vascular stents and grafts.

Luminal prostheses are provided for a variety of medical purposes. For example, luminal stents can be placed in various body lumens, such as blood vessels, the ureter, urethra, biliary tract, and gastrointestinal tract, for maintaining patency. Luminal stents are particularly useful for placement in atherosclerotic sites in blood vessels or fistula or bypass grafts. Luminal grafts can be placed in blood vessels to provide support in diseased regions, such as aortic abdominal, and other aneurysms.

Both stent and graft prostheses must meet certain mechanical criteria to function successfully. In particular, such prostheses should be at least partly flexible or articulated (i.e., adjacent expansible ring segments are connected by links that articulate relative to one another) over their lengths so that they may be advanced through tortuous body lumens, such as those of the coronary vasculature. In addition, the prostheses should have controllable length change properties, either to maintain their original length or to have the ability to elongate or foreshorten, as desired, when the prostheses assume an expanded configuration. Further such prostheses must have sufficient mechanical strength, particularly hoop strength after they are expanded, in order to mechanically augment the luminal wall strength and thus maintain lumen patency. The ability to meet these requirements is severely limited in the case of stents and grafts which are delivered in a radially constrained or collapsed configuration. Such prostheses must radially expand at a target site within the body lumen, so any adaptations which are intended to enhance flexibility must not interfere with the ability to radially expand or to maintain strength once expanded.

Prior luminal prostheses often have structures which present a risk of injury as they are endoluminally delivered (i.e., tracked) to and/or released at a target site within a patient's body lumen. In particular, many vascular stents comprise a plurality of circumferentially connected and spaced-apart ring segments which deform circumferentially as the stent is radially expanded. The Palmaz stent described in U.S. Pat. Nos. 5,102,417 and 4,776,337, is typical of such stents. Such stent designs can present challenges in both delivery and deployment. For example a phenomenon called "flaring" occurs when the longitudinal elements of the distal or proximal end of the prosthesis are bent outward to assume a crown-like configuration due to bending forces placed on these elements as the prosthesis passes through tortuous body passageways. Flaring can create the same deleterious effects as the previously described fish scaling phenomenon, injuring or traumatizing the blood vessel wall as the prosthesis is delivered or tracked within the blood vessel. In addition, flaring may increase a tendency for stent movement relative to a delivery balloon, thus causing an improperly deployed stent or, possibly, dislodging the undeployed stent completely from the catheter.

In addition to challenges during delivery, prior luminal prostheses can suffer problems during expansion, particularly during balloon expansion of malleable stents. For example, it has been found that balloon expansion of vascular stents often results in the ends of the stent expanding preferentially compared to the center of the stent. Such "dog-bone" expansion inhibits sufficient expansion of the center or ends of the stent, thus leaving a restricted luminal area in the fully deployed stent. Conversely, sometimes it will be desired to flare the ends of the stent in order to lock the stent in place and prevent the ends of the stent from collapsing after deployment. The ability to program stent expansion over the length of the stent has generally been lacking in prior stent designs.

A still further problem experienced by many prior stent designs is a lack of vessel coverage after expansion. It will be appreciated that the ability to support luminal patency and inhibit hyperplasia and other luminal in-growth can be enhanced if relative coverage of the luminal wall area by the expanded stent is increased. Thus, stent designs which afford a greater luminal wall coverage, or which minimize the free space between stent structures, while minimizing the amount of stent material used may be advantageous. Such increase of luminal wall coverage, however, should not be achieved at the expense of "crimpability." Particularly for vascular applications, it is desirable that the diameter of the stent be reduced as much as possible during delivery, e.g., when crimped over a delivery balloon. By minimizing the crimped-stent diameter, both trackability and the ability to cross smaller lesions and access more distal lesions will be enhanced. In addition, a larger crimped-stent diameter may increase the risk of stent movement relative to the deployment balloon which, in turn, could cause an improperly deployed stent or even loss of the undeployed stent from the catheter. The ability to reduce the stent diameter is generally limited by the amount of material in the stent itself. Thus, designs which increase the ability of the stent to cover the luminal wall without significantly reducing the "crimpability" would be particularly desirable.

For these reasons, it would be desirable to provide improved stent, graft, and other luminal prostheses. In particular, it would be desirable to provide improved luminal prostheses which exhibit a high degree of flexibility with minimum losses of hoop strength and luminal wall coverage after the prostheses are expanded. For example, the design should be such that the expanded prostheses will conform to both curved and straight vessels with minimal or no straightening or other unintended deformation of the vessel wall. Such luminal prostheses should be trackable, preferably being both flexible and presenting minimum risk of injury to the luminal wall as they are being delivered. In particular, the prostheses should avoid "fish scaling" and should be highly "crimpable" so that the prostheses diameter during delivery can be reduced. The luminal prostheses will preferably further display superior expansion characteristics. In particular, the prostheses designs should permit selective programming of the expansion characteristics along the length of the prostheses. For example, the designs should permit preferential expansion over the central portion of the prosthesis, or alternatively at either or both ends of the prostheses depending on the particular application in which the prosthesis is to be used. Still further preferably, upon expansion the prostheses should display superior luminal wall coverage and adequate to superior hoop strength in order to best maintain patency of the body lumen being treated. At least some of these objectives will be met by the luminal prostheses described and claimed hereinafter.

2. Description of the Background Art

Stents having expansible ring segments joined by sigmoidal links and axial beams are described in WO 99/17680. Stents comprising expansible rings including struts and hinges where the hinges are configured to have different opening forces are described in U.S. Pat. No. 5,922,020. EP 662 307 describes an expansible stent having serpentine elements with varying degrees of curvature to provide controlled expansion characteristics. WO 00/003662 describes a stent delivery balloon which preferentially opens a center region of a stent as the balloon is expanded. U.S. Pat. No. 6,017,365, describes a stent with serpentine segments with non-linear struts and sigmoidal links. Other patents of interest include U.S. Pat. Nos. 4,776,337; 5,102,417; 6,017,362; 6,015,429; and 6,013,854.

SUMMARY OF THE INVENTION

The present invention provides improved luminal prostheses suitable for endoluminal placement within body lumens, particularly blood vessels, and most particularly coronary and peripheral arteries. The luminal prostheses may be in the form of stents, intended for maintaining luminal patency, or may be in the form of grafts, intended for protecting or enhancing the strength of a luminal wall. Generally, the term "stent" will be used to denote a vascular or other scaffold structure comprising expansible components, such as ring segments, which when expanded form an open lattice or framework which is disposed against the luminal wall. In contrast, the term "graft" will generally denote such as luminal scaffold which is covered by a liner, membrane, or other permeable or impermeable layer which covers at least a portion of the scaffold. The drawings included herein are generally directed at stent structures, but it will be appreciated that corresponding graft structures could be provided by incorporating a liner, membrane, or the like, on either the outer or inner surfaces of the stent.

The luminal prostheses of the present invention will be radially expansible, usually by the application of a radially outward internal force to expand a minimally resilient (usually malleable) prosthesis structure. Such radially outward internal force will usually be provided by an inflatable balloon, and such balloon expansible stents are well-known in the art and described in the background references which have been cited above and are incorporated herein by reference. Alternatively, at least some of the radially expansible luminal prostheses of the present invention may be self-expanding. By fabricating the prostheses from a resilient material, usually a metal, such as spring stainless steel, a nickel-titanium alloy (such as Nitinol® alloy), or the like, the prosthesis can be designed to have a large (fully expanded) diameter in an unconstrained state. The diameter of the prosthesis can be reduced by applying a radial constraint, e.g., by placing the prosthesis within a sleeve, tube, or other constraining structure. In that way, the self-expanding prosthesis can be delivered while constrained and deployed by releasing the constraint at the target site within the body lumen. The general principles of constructing self-expanding stents and other luminal prostheses are also well-known in the art and described in at least some of the background references which have previously been incorporated herein.

In a first aspect of the present invention, a radially expansible luminal prostheses comprises a plurality of serpentine ring segments including struts connected by hinge regions. The struts may be straight or may have non-linear configurations, e.g., being curved, wavy, or the like. The use of non-linear struts may be advantageous in order to increase the area of the strut which engages the luminal wall after expansion without significantly reducing flexibility and/or crimpability of the strut. The hinge regions are usually formed by a short curved or C-shaped region which permits the connected struts to reverse direction in order to define the serpentine ring pattern. Adjacent serpentine rings are joined by sigmoidal links, i.e., S-shaped elements which may be malleable or elastically deformable in order to allow the adjacent segments to flex relative to each other during prosthesis delivery and expansion. The sigmoidal links are attached to a side of the hinge region, typically located at the point where the hinge attaches to or transforms into the strut. The use of such sigmoidal links is beneficial since it permits the longitudinal expansion or contraction of the prosthesis to accommodate length changes as the prosthesis is expanded. Such links further permit bending of the prosthesis since they allow differential motion of adjacent serpentine rings. Such flexibility is particularly advantageous since it allows improved tracking of the prosthesis as it is delivered to an endoluminal location. The sigmoidal links also improve the conformability of the expanded prosthesis when placed in a native vessel, artificial graft, or other body lumen location. Such a structure distinguishes prior art designs where a sigmoidal link is attached at or near the apex of the link. By attaching the sigmoidal link closer to the strut, the adjacent ring segments can be positioned closer to each other. Moreover, because the links attach away from the apex of the hinge region, stress at the apex is reduced and uniform expansion of each ring segment is enhanced.

In a second aspect of the present invention, the apexes of opposed hinge regions on adjacent serpentine rings will be circumferentially offset. That is, the hinge regions apices on at least some (often all) of the serpentine rings will be aligned with the trough regions on the adjacent serpentine ring. In this way, the hinge regions are circumferentially offset so that the circumferential length of the sigmoidal links connecting proximate hinge regions can be reduced. Such a design also allows for adjacent serpentine rings to be closer together to allow for improved vessel coverage upon prosthesis expansion. Such a design also permits an increase in the diameter of the curved portions of the sigmoidal link which further improves stress distribution and opening characteristics of the prosthesis. Preferably, the luminal prostheses of the present invention will both have the sigmoidal links attached to the sides of the hinge regions and have the hinge regions circumferentially offset in order to achieve the greatest improvement in flexibility, crimpability, and uniform expansion characteristics.

The sigmoidal links will preferably have a S-shaped geometry with two outer connecting legs joined to a central leg by U-shaped joints. In some instances, it might also be possible to provide Z-shaped sigmoidal links, but those will generally be less preferred. In connecting the sigmoidal links to the hinge regions of the serpentine rings, the outer connecting legs will generally be oriented in the annular or circumferential direction and attach to the hinge region on its side.

In a further aspect of the present invention, a radially expansible luminal prosthesis comprises a plurality of ring segments which are expansible in response to a radially outward force. The ring segments may comprise serpentine rings, as generally described above, or may comprise zig-zag segments, box segments, or other conventional prosthesis ring patterns. The expansion characteristics of the luminal prosthesis may be varied over the length of the prostheses by controlling or programming the characteristics of each of the adjacent expansible ring segments. For example, different ring segments can be controlled to have different cross-sectional areas, e.g., differing widths, thicknesses or both, so that the amount of radially outward force needed to open the stent is lesser or greater. Alternatively, in the case of serpentine or zig-zag ring patterns, the strut length may be varied in order to control the force needed to open the stent. That is, ring segments having a greater strut length will open with a lesser force since the increased strut length will leverage the force applied to a hinge region so that the hinge region will open sooner. Other techniques for controlling the expansion characteristics of an individual ring segment may also be employed, such as those described in U.S. Pat. No. 5,922,020, the full disclosure of which has previously been incorporated herein by reference. Depending on the objective, the ring segments near either or both ends of the prosthesis may be programmed to open more or less readily so that, when applying a constant radially outward force along the length of the prosthesis, the stent will first open either at both ends or in the middle. It will be appreciated that by employing balloons which also have variable expansion characteristics, such as those described in WO 00/03662, a wide variety of prosthesis expansion characteristics can be provided over the length of the prosthesis.

DESCRIPTION OF THE SPECIFIC EMBODIMENTS

The present invention provides luminal prostheses intended for endoluminal placement in body lumens, particularly within the vascular system for the treatment of cardiovascular disease, such as vascular stenoses, dissections, aneurysms, and the like. The prostheses, however, are also useful for placement in other body lumens, such as the ureter, urethra, biliary tract, gastrointestinal tract and the like, for the treatment of other conditions which may benefit from the introduction of a reinforcing or protective structure within the body lumen.

The prostheses are preferably placed endoluminally. As used herein, "endoluminally" will mean placement through a body opening or by percutaneous or cutdown procedures, wherein the prosthesis is translumenally advanced through the body lumen from a remote location to a target site in the lumen. In vascular procedures, the prostheses will typically be introduced "endovascularly" using a catheter over a guidewire under fluoroscopic guidance. The catheters and guidewires may be introduced through conventional access sites to the vascular system, such as through the femoral artery, or brachial, subclavian or radial arteries, for access to the coronary arteries.

A luminal prosthesis according to the present invention will usually comprise at least two radially expansible, usually cylindrical, ring segments. Typically, the prostheses will have at least four, and often five, six, seven, eight, ten, or more ring segments. At least some of the ring segments will be adjacent to each other but others may be separated by other non-ring structures.

By "radially expansible," it is meant that the segment can be converted from a small diameter configuration (used for endoluminal placement) to a radially expanded, usually cylindrical, configuration which is achieved when the prosthesis is implanted at the desired target site. The prosthesis may be minimally resilient, e.g., malleable, thus requiring the application of an internal force to expand and set it at the target site. Typically, the expansive force can be provided by a balloon, such as the balloon of an angioplasty catheter for vascular procedures. As will be described below, the present invention preferably provides sigmoidal links between successive unit segments which are particularly useful to enhance flexibility and crimpability of the prosthesis.

Alternatively, the prosthesis can be self-expanding. Such self-expanding structures are provided by utilizing a resilient material, such as a tempered stainless steel or a superelastic alloy such as a Nitinol® alloy, and forming the body segment so that it possesses its desired, radially-expanded diameter when it is unconstrained, i.e. released from the radially constraining forces of a sheath. In order to remain anchored in the body lumen, the prosthesis will remain partially constrained by the lumen. The self-expanding prosthesis can be tracked and delivered in its radially constrained configuration, e.g., by placing the prosthesis within a delivery sheath or tube and removing the sheath at the target site.

The dimensions of the luminal prosthesis will depend on its intended use. Typically, the prosthesis will have a length in the range from about 5 mm to 100 mm, usually being from about 8 mm to 50 mm, for vascular applications. The small (radially collapsed) diameter of cylindrical prostheses will usually be in the range from about 0.5 mm to 10 mm, more usually being in the range from 0.8 mm to 1.25 mm for vascular applications. The expanded diameter will usually be in the range from about 1.5 mm to 50 mm, preferably being in the range from about 2.5 mm to 30 mm for vascular applications.

The ring segments may be formed from conventional materials used for body lumen stents and grafts, typically being formed from malleable metals, such as 300 series stainless steel, or from resilient metals, such as superelastic and shape memory alloys, e.g., Nitinol® alloys, spring stainless steels, and the like. It is possible that the body segments could be formed from combinations of these metals, or combinations of these types of metals and other non-metallic materials. Additional structures for the body or unit segments of the present invention are illustrated in U.S. Pat. Nos. 5,195,417; 5,102,417; and 4,776,337, the full disclosures of which are incorporated herein by reference.

Figure 1A:
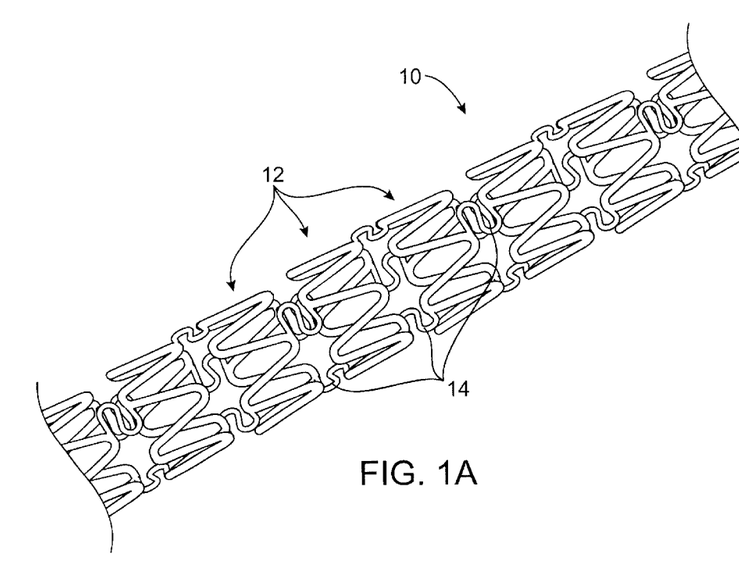
FIGS. 1A and 1B are digital photographs of a coronary stent constructed in accordance with the principles of the present invention with FIG. 1A showing the stent in an unexpanded configuration and FIG. 1B showing the stent in an expanded configuration.
Figure 1B:
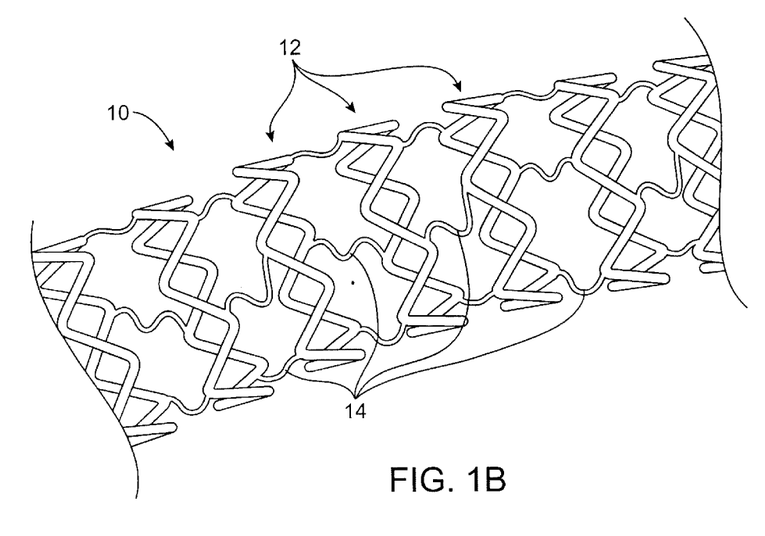

Referring now to FIGS. 1A and 1B, an exemplary luminal prosthesis 10 particularly intended for implantation in the coronary vasculature comprises from 4 to 50 ring segments 12 (with 7 being illustrated). Each ring segment 12 is joined to the adjacent ring segment by at least one of sigmoidal links 14 (with three being illustrated). Each ring segment 12 includes a plurality, e.g., six, strut/hinge units (described in more detail in connection with FIGS. 2–5 below), and two out of each six hinge/strut structures on each ring segment 12 will be joined by the sigmoidal links 14 to the adjacent ring segment. FIG. 1A shows the prosthesis 10 in a collapsed or narrow diameter configuration while FIG. 1B shows the prosthesis in its expanded configuration.

Figure 2:
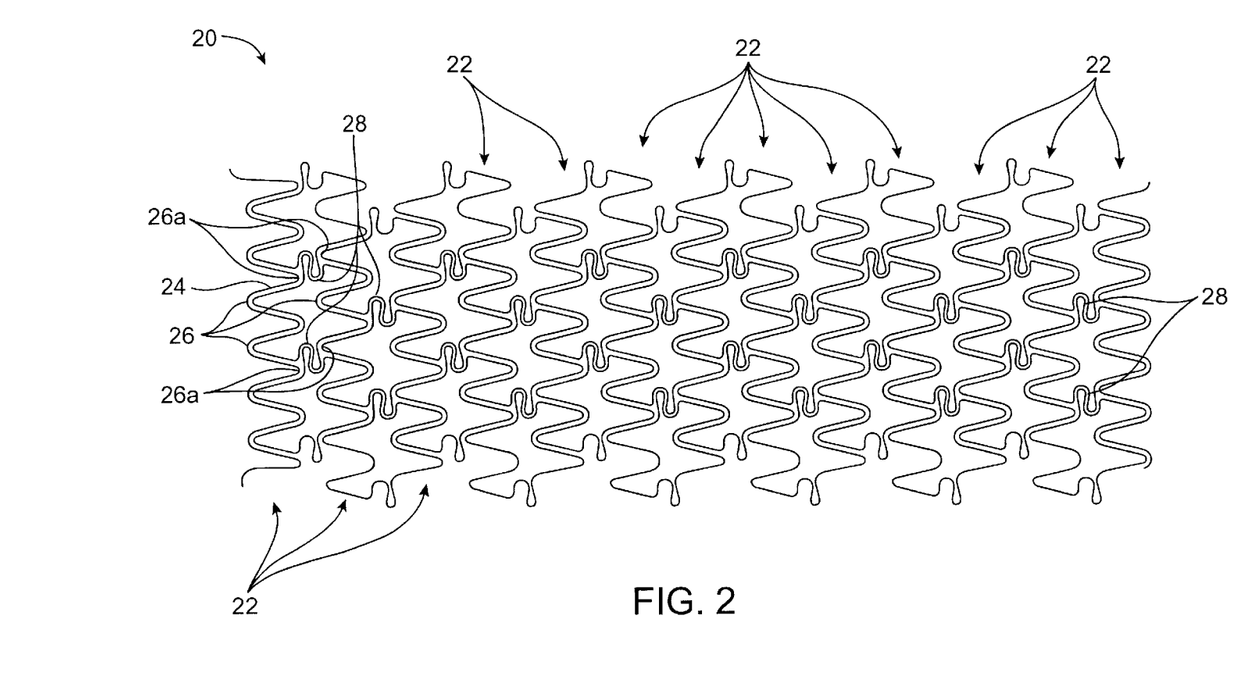
FIG. 2 is a "rolled out" view of a the exemplary scaffold structure of FIGS. 1A and 1B.
Figure 4:
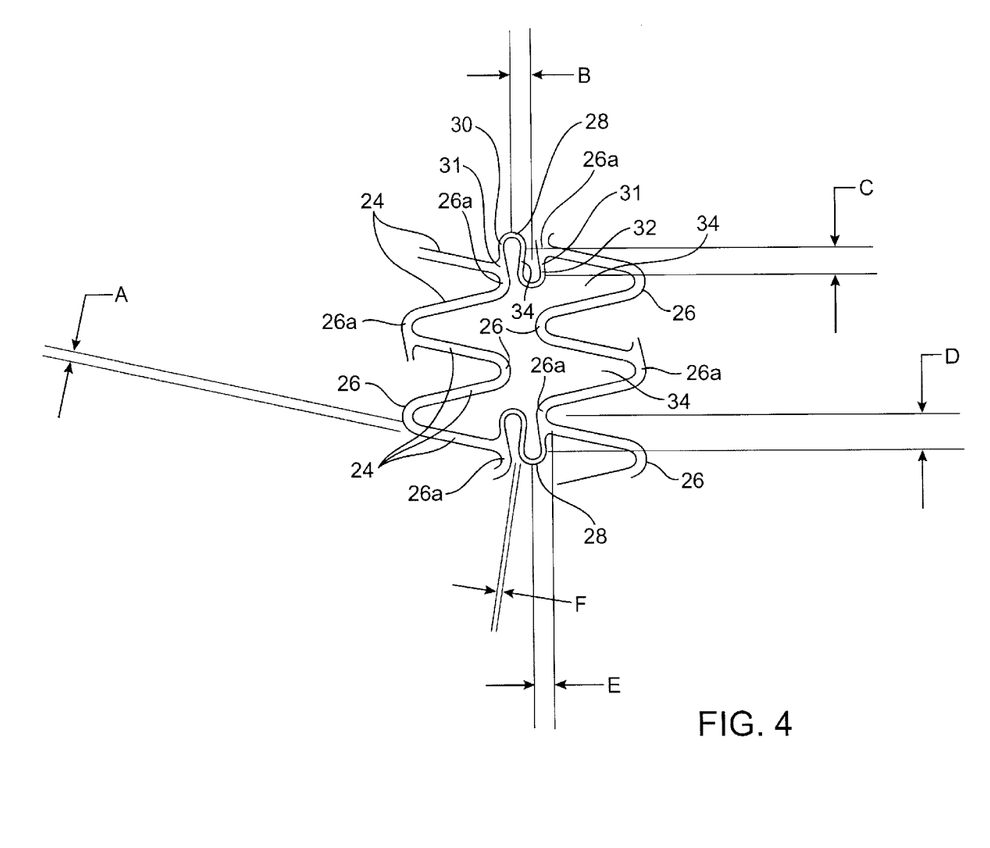
FIG. 4 is a detailed view of the scaffold structure of FIG. 2 showing preferred dimensions of the scaffold components.

Referring now to FIGS. 2 and 4, a first embodiment of a luminal prosthesis 20 constructed in accordance with the principles of the present invention will be described in detail. The prosthesis 20 comprises serpentine ring segments 22, where each ring segment has essentially identical characteristics. The ring segments 22 comprise a plurality of linear struts 24 joined by curved hinge regions 26 and 26a. As illustrated also in FIG. 4, the hinge regions 26 are free from other structure, i.e., they are not linked to adjacent hinge regions or other prosthesis structure. The hinge regions 26a, in contrast, are connected or joined to sigmoidal links 28 which secure the adjacent ring segments 22. In the embodiment of FIG. 2, each adjacent serpentine ring segment 22 is joined by three sigmoidal links 28. The number of lengths, however, could vary from one, two, up to the total number of hinge regions, i.e., six in the illustrated embodiment of FIG. 2.

The sigmoidal links 28 are adjoined to the hinge regions 26a so that a first outer leg segment 30 connects to the hinge region at its base i.e., where the hinge opens into the strut 24. Similarly, a second outer leg segment 32 is joined to hinge region 26a on the adjacent serpentine ring 22 at the base of that hinge region. The legs 30 and 32 are generally oriented in a circumferential or annular direction at the point where they attach to the hinge regions 26a. The legs are joined by a pair of U-shaped regions which join a central leg 34 to complete the sigmoidal link. This design of the sigmoidal link has a number of advantages. For example, by orienting the leg segments 30 and 32 circumferentially, the legs can move circumferentially past each other to accommodate radial crimping of the prosthesis as well as facilitate radial opening of the stent. Additionally, the structure permits axially shortening and elongation to permit bending of the prosthesis as it is being introduced through tortuous regions of a blood vessel or other body lumen.

As also best seen in FIG. 4, the serpentine ring segments 22 are rotationally oriented relative to each other so that the apices on the hinge regions 26 and 26a on the first ring segment are aligned with a trough region 34 on the adjacent ring segment. Such relative rotational alignment of the ring segments 22 minimizes the circumferential length of the sigmoidal links 28 need to connect the opposed hinge regions. It will be appreciated that if the apices of opposed hinge regions 26 and 26a were rotationally aligned, the length of the connecting leg 34 would have to be significantly longer. Minimizing the length permits optimum configuration of the sigmoidal link. By minimizing the length of the connecting legs of the sigmoidal link, the crimped diameter can be minimized as the sigmoidal links will not be interfering with the crimped configuration. In addition, by having shorter connecting legs on the sigmoidal link, the gaps between adjacent ring segments on the expanded prosthesis will be minimized. Preferably, leg segments 30 and 32 each have flared ends 31 and 33, respectively, which connect the sigmoidal link 28 to the adjoining hinge region 26a. The flared ends provide stress relief as the ring segments 22 and links 28 are expanded.

The dimensions of the hinges, struts, sigmoidal links, and the like, of the luminal prostheses of the present invention may vary considerably depending on the intended use. Exemplary dimensions intended for a coronary stent (FIG. 4) are set forth in Table I below.

TABLE I

| | Exemplary Dimensions (mm) | | |
|---|---|---|---|
| | A | B | C |
| Broad Range | 0.025 to 1.25 | 0 to 6.5 | 0.075 to 1.25 |
| Preferred Range | 0.075 to 0.15 | 0.15 to 0.25 | 0.2 to 0.4 |
| | D | E | F |
| Broad Range | 0.1 to 6.5 | 0 to 6.5 | 0.025 to 0.65 |
| Preferred Range | 0.25 to 0.5 | 0.15 to 0.3 | 0.035 to 0.075 |

Figure 3A:
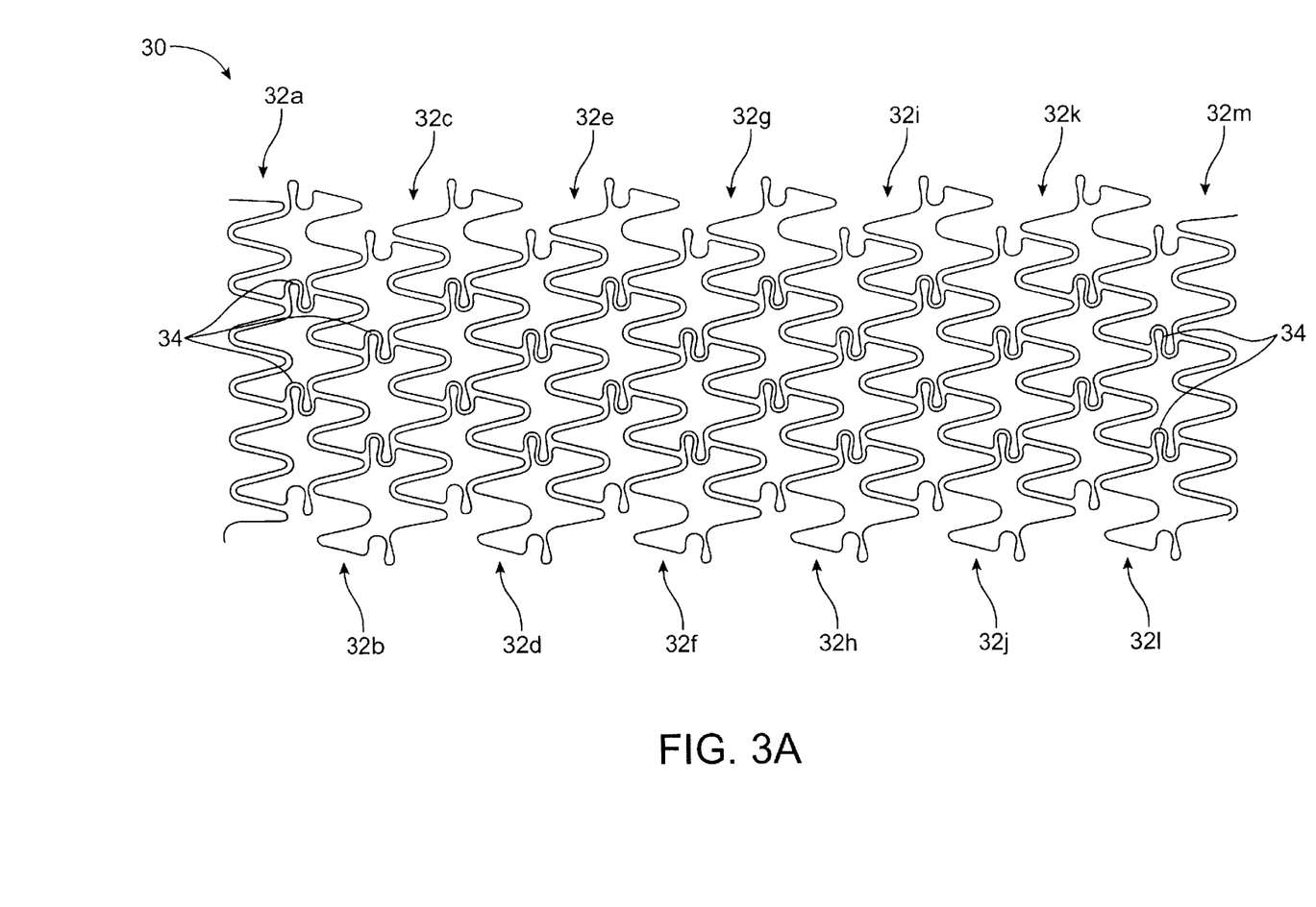
FIGS. 3A through 3C are "rolled out" views of second through fourth exemplary embodiments of scaffold structures which may be programmed to display differential expansion characteristics over the length of the prosthesis.
Figure 3B:
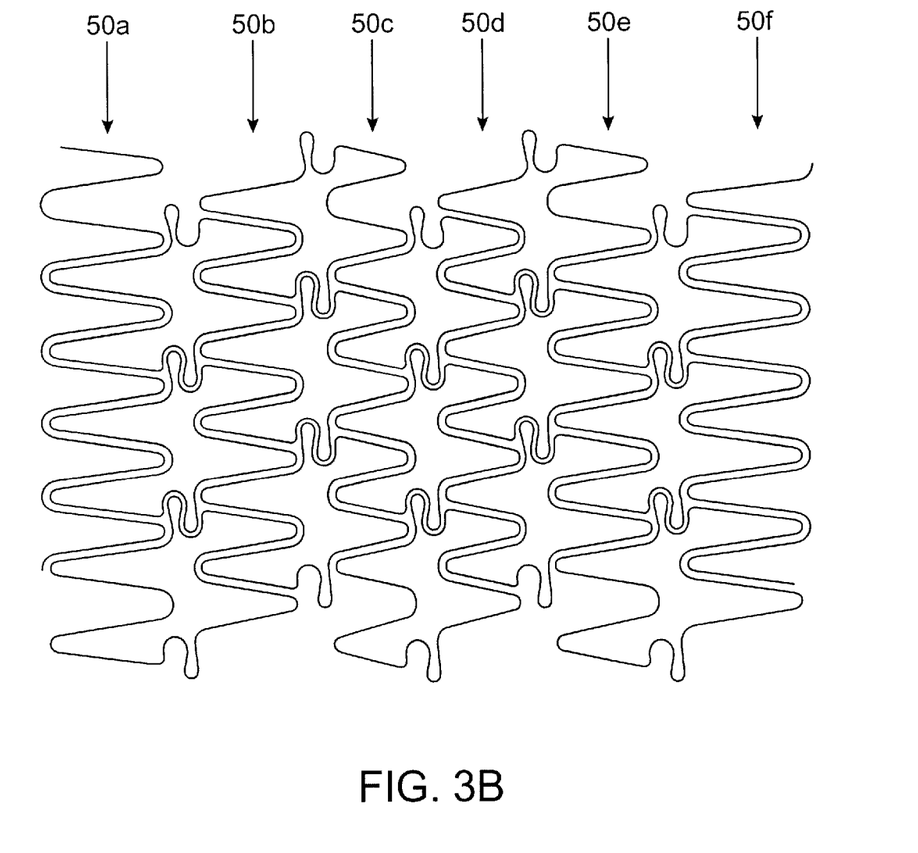
Figure 3C:
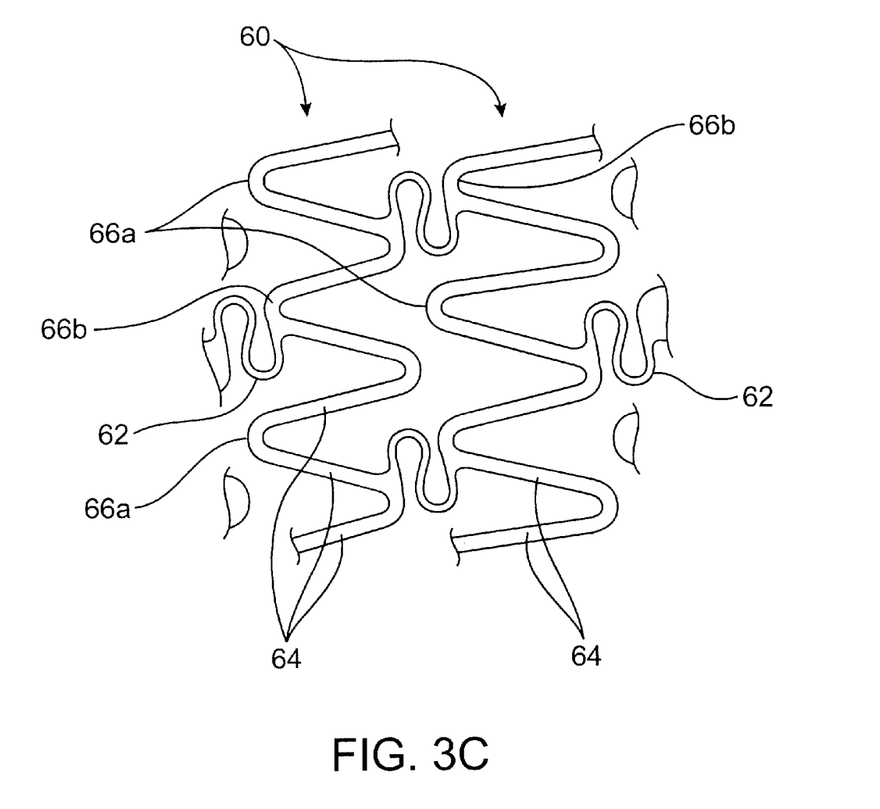

Referring now to FIGS. 3A through 3C, embodiments of the luminal prostheses of the present invention where adjacent serpentine ring segments have different expansion characteristics will be described. In FIG. 3A, a luminal prosthesis 30 has a plurality of adjacent serpentine ring segments 32a–32m. Individual serpentine ring segments 32a–32m will have different expansibility characteristics so that the prosthesis 30 will differentially open along its length in response to uniform opening forces. The expansibility characteristics of the individual ring segments may be modified in a number of the different ways. In a first general approach, the yield profile(s) of some or all of the hinges in an individual ring segment can be modified relative to such profiles for others of the ring segments. This can be done by increasing or decreasing the width, thickness, or other cross-sectional dimension of any one or more of the hinge regions. Alternatively, the lengths of the struts connecting the hinge regions can be increased or decreased to change the leveraged force applied to a hinge region when the prosthesis is being expanded by an internal radially outward force. Other approaches, such as adjusting the radius of an arcuate hinge region are also known.

Figure 4A:
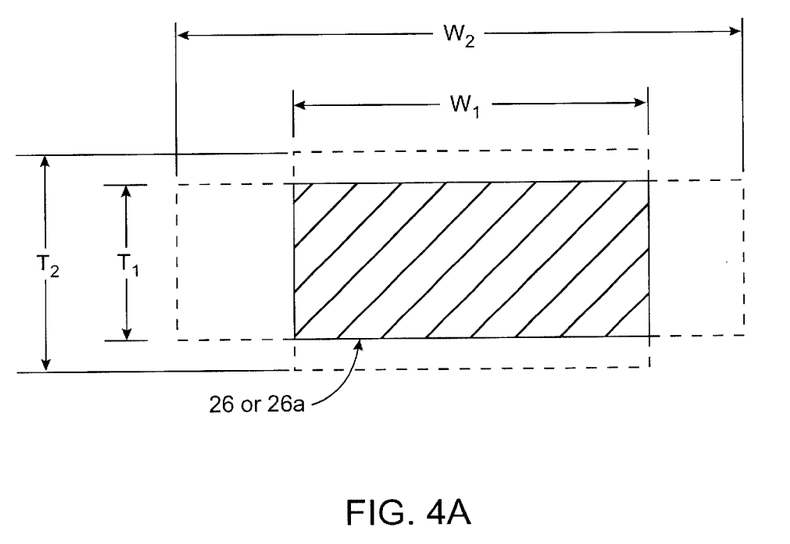
FIG. 4A is a cross-sectional view of a hinge region of a scaffold structure of the present invention.

FIG. 4A is a cross-sectional view of the hinge region 26 or 26a having a width W and a thickness T. A hinge region 26 or 26a having a smaller width W, and/or a smaller thickness T, will have less resistance to opening than a hinge region which has a larger thickness $T_2$ and/or a small width $W_2$. Thus, as described above, the opening characteristics of the prosthesis can be programmed by adjusting the widths and/or thickness of the hinge regions in particular ring segments 22.

Figure 7A:
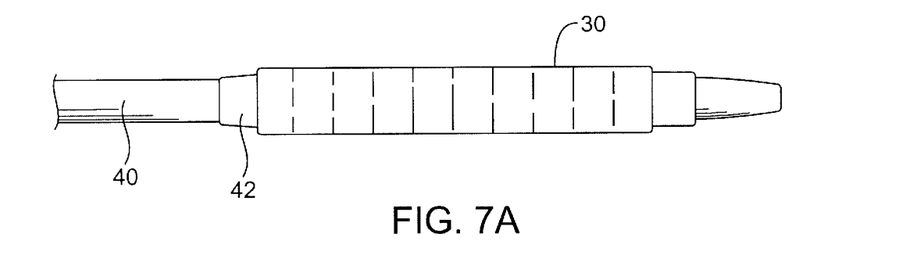
FIGS. 7A–7C show balloon expansion of a luminal prosthesis, such as that having the scaffold structure of FIG. 3A or FIG. 3B, which has been programmed so that it preferentially expands near its center.
Figure 7B:
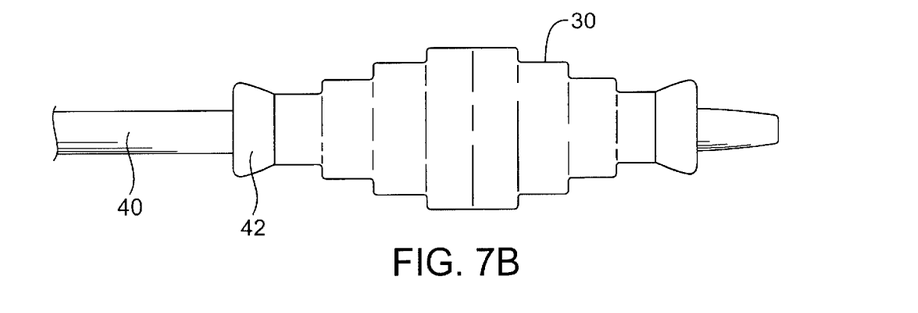
Figure 7C:
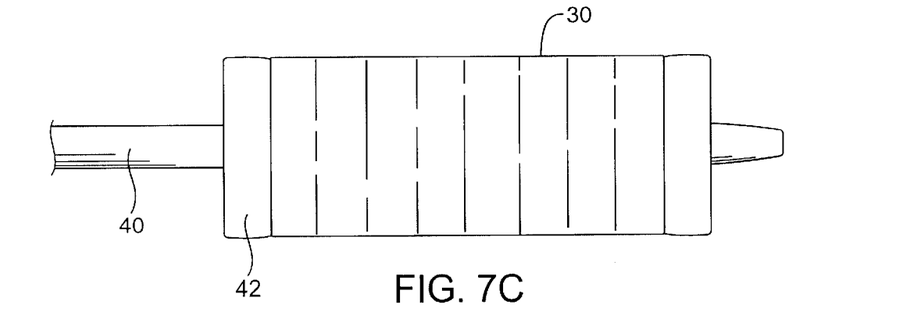

In the particular embodiment of FIG. 3A, the serpentine ring segments 32a–32c and 32k–32m have struts and hinge regions with a larger width than those of the middle ring segments of 32d–32j. The innermost ring segments 32f–32h have the smallest widths for the struts and hinge regions. Thus, assuming the prosthesis 30 is formed from the same material (or different materials having the same mechanical properties) over its entire length, the hinges of the ring segments 32 having greater widths will be stiffer and provide more resistant to expansion. In contrast, the ring segments having the narrowest widths (32f–32h) will be the least stiff and have the least resistance to expansion in response to an internally applied force. Thus, when the prosthesis 30 is expanded over a balloon 42 on a balloon catheter 40, the prosthesis will preferentially expand over the central region, as illustrated in FIG. 7A–7C. In particular, the prosthesis 30 is shown in FIG. 7A prior to expansion. As the balloon 42 is partially expanded (FIG. 7B), the prosthesis 30 begins opening in its middle sections prior to its end sections. Finally, after the balloon is fully expanded (FIG. 7C), uniform expansion of the prosthesis 30 along its length can be achieved. Of course, when expanded in a body lumen, full expansion of the prosthesis 30 may be constrained so that the center sections will first engage the wall with the end sections engaging the wall at a later time. Such deployment may be advantageous since it assures that the central regions of the prosthesis are filly engaged against the luminal wall prior to opening of the end portions.

Under other circumstances, however, it may be desired to preferentially open the end portions of the luminal prosthesis first. In such instances, the luminal prosthesis 30 could be modified so that the end segments 32a–32c and 32k–32m open preferentially with respect to the central ring segments 32d–32j. A variety of other opening characteristics, such as tapered would also be possible. For example, a tapered opening could be achieved by providing a stiffness gradient where segments at one end, such as 32a, are the least stiff with ring segments becoming progressively stiffer in the direction of ring segment 32m.

Differential expansion of different ring segments can be achieved in a variety of ways. For example, as shown in FIG. 3B, instead of selecting different widths or other cross-sectional dimensions for the hinge regions of the ring segment, the strut length could be varied. As shown in FIG. 3B, the struts in end segments 50a and 50f are the longest, with the strut lengths in the inner ring segments 50b–50e becoming progressively shorter. Ring segments having longer strut lengths will apply a greater force to the hinge regions of those struts in response to an equal radially outward expansion force. Thus, as shown in FIG. 3B, the end ring segments 50a and 50f will preferentially open with respect to the inner ring segments 50b–50e. Still further ways for controlling the expansion characteristics of an individual ring segment could also be utilized. For example, the hinge regions could be weakened and/or strengthened, as described in detail in U.S. Pat. No. 5,922,020. Alternatively, the diameters of the hinge regions could be varied in successive ring segments, as described generally in European patent application 662 307.

Referring now to FIG. 3C, serpentine ring segments 60 can be programmed to have different expansion rates by adjusting the lengths of some, but not all, of the struts 64 in any ring. The serpentine rings 60 will be joined by sigmoidal links 62, generally as described above. Rather than having struts 64 with identical lengths, those struts which terminate in hinges 66a which are not adjacent to the sigmoidal links 62 can be made longer than those struts 66b which are adjacent the sigmoidal links. This ability offers an additional degree of freedom in programming the expansion rates of the individual serpentine rings as well as the overall prosthesis made from such rings.

Figure 5:
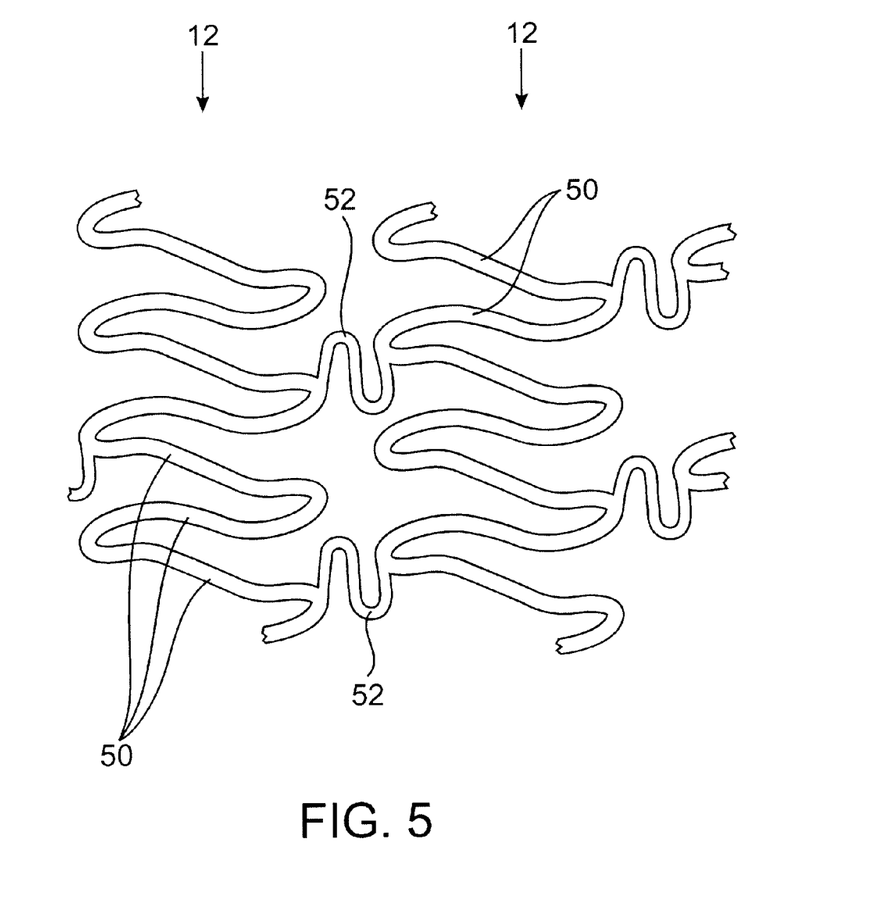
FIG. 5 is a detailed view similar to FIG. 4, showing the optional incorporation of non-linear struts into the scaffold structure.

In an optional aspect of the present invention, at least some of the serpentine ring segments may employ non-linear struts. As shown in FIG. 5, ring segments 12 may comprise non-linear struts 50 which are joined by sigmoidal links 52 in a manner described above in connection with other embodiments of the present invention. The use of non-linear struts is advantageous in that it increases the length and therefore the amount of strut available for engagement against a luminal wall without increasing the length of the prosthesis. The ability to increase the coverage of the stent against the luminal wall is well recognized in the art. In addition, the use of non-linear struts can reduce the crimped-stent diameter since the wall thickness of the stent itself can be decreased without loss of expanded hoop strength. Another advantage of a non-linear strut design is that it increases the amount of material within the strut thus improving upon the fluoroscopy characteristics of the stent.

Figure 6A:
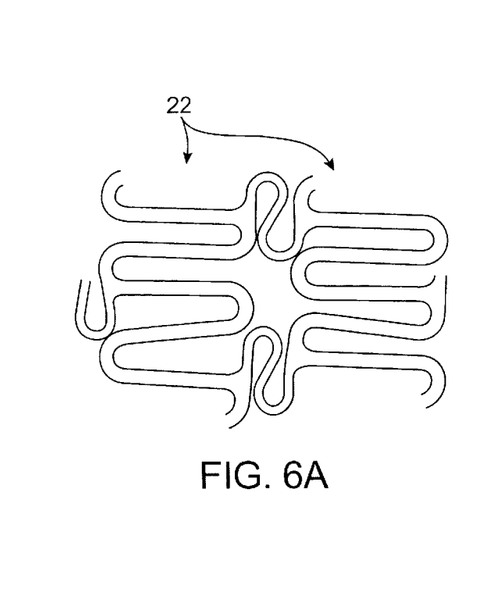
FIGS. 6A and 6B are detailed views showing the scaffold structure of FIG. 2 in its non-expanded configuration (FIG. 6A) and in its fully expanded configuration (FIG. 6B).
Figure 6B:
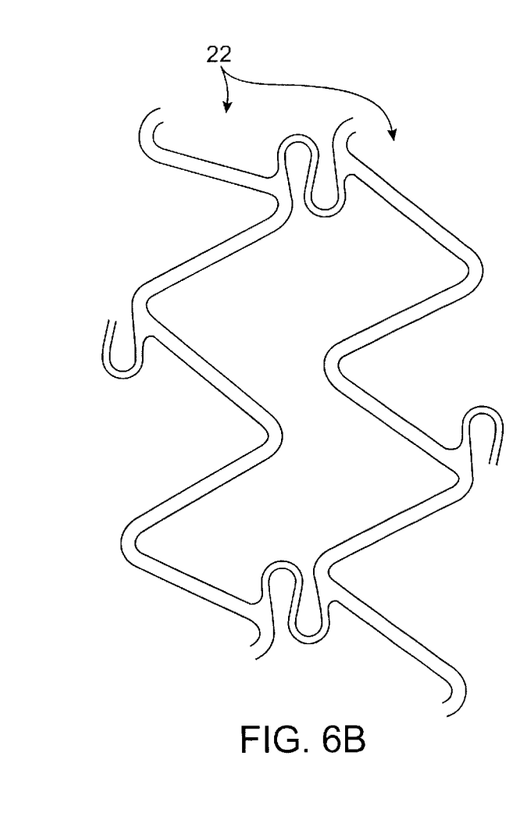

Referring now to FIG. 6A and 6B, the improved expansion characteristics of the luminal prosthesis 20 of FIG. 2 will be described. It is assumed that the prosthesis 20 has been placed over a delivery balloon and that a constant expansion force over the length of the prosthesis is being applied. FIG. 6A and 6B show a detailed section of two adjacent serpentine rings 22, with the prosthesis shown in its fully collapsed or crimped condition in FIG. 6A and its fully expanded condition in FIG. 6B. As pressure is applied to the delivery balloon, an outward radial force is applied to the prosthesis. This radial force causes the hinge regions of the serpentine rings to flex open as the prosthesis is expanded. For a material such as stainless steel, the stresses within the hinge region become higher than the yield strength and enter the plastic region of the material. This allows the prosthesis to remain open following removal of the delivery balloon. For a shape-memory or other resilient alloy, such as Nitinol®, the natural state of the prosthesis is in the expanded configuration. For such "self-expanding" designs, a sheath is holding the prosthesis in a crimped configuration for delivery to the lesion site. Once the desired deployment location has been reached, the sheath is retracted and the prosthesis is expanded to its natural position. The hinges act as springs in causing such expansion.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A radially expansible luminal prosthesis comprising scaffold consisting essentially of:
   a plurality of serpentine ring segments including struts having hinge regions being circumferentially offset with axially proximate apices and side regions disposed on either side of the apices; and
   sigmoidal links between hinge regions on adjacent serpentine rings and attached on a side of the hinge regions;
   wherein an imaginary line bisecting an angle at an apex formed between two adjoining struts is parallel to a longitudinal axis of the prosthesis; and
   wherein each serpentine ring segment and the adjacent sigmoidal links form a cell and wherein each cell is substantially similar in shape.

2. A radially expansible luminal prosthesis as in claim 1, wherein each sigmoidal link comprises two connecting legs and wherein each connecting leg is attached to a hinge region in a circumferential direction.

3. A radially expansible luminal prosthesis as in claim 2, wherein each sigmoidal link has a uniform width over its length.

4. A radially expansible luminal prosthesis as in claim 2, wherein each sigmoidal link has a flared end which joins to the hinge region.

5. A radially expansible luminal prosthesis as in claim 2, wherein the sigmoidal link is adapted to permit the connecting legs to move circumferentially past each other to accommodate radial crimping of the prosthesis.

6. A radially expansible luminal prosthesis as in claim 1, wherein the ring segments are expansible in response to a radially outward force; wherein at least one of the ring segments opens at a different rate or in a different amount than at least one other ring segment when exposed to the same radially outward force.

7. A radially expansible luminal prosthesis as in claim 6, wherein at least some struts in at least some of the serpentine rings have different lengths to cause a different rate or amount of expansion.

8. A radially expansible luminal prosthesis as in claim 7, wherein at least some struts which are positioned away from the sigmoidal links are longer.

9. A radially expansible luminal prosthesis as in claim 6, wherein at least some of the struts have different widths than others of the struts to cause a different rate or amount of expansion.

10. A radially expansible luminal prosthesis as in claim 5, wherein at least some of the hinge regions have different widths than others of the hinges regions to cause a different rate or amount of expansion.

11. A radially expansible luminal prosthesis as in claim 1, wherein at least some of the struts are straight over the distance between the hinges.

12. A radially expansible luminal prosthesis as in claim 1, wherein at least some of the struts are non-linear.

13. A radially expansible luminal prosthesis as in claim 1, wherein the sigmoidal links are individually axially expansible and contractable.

14. A radially expansible luminal prosthesis comprising a scaffold consisting essentially of:
   a plurality of serpentine ring segments including struts having hinge regions being circumferentially offset with axially proximate apices and side regions which are disposed on either side of the apex; and
   sigmoidal links between hinge regions and comprising two connecting legs with each connecting leg attached in a circumferential direction to a side of the hinge regions;
   wherein an imaginary line bisecting an angle at an apex formed between two adjoining struts is parallel to a longitudinal axis of the prosthesis; and
   wherein each serpentine ring segment and the adjacent sigmoidal links form a cell and wherein each cell is substantially similar in shape.

15. A radially expansible luminal prosthesis as in claim 14, wherein each sigmoidal link has a uniform width over its length.

16. A radially expansible luminal prosthesis as in claim 14, wherein each sigmoidal link has a flared end which joins to the hinge region.

17. A radially expansible luminal prosthesis as in claim 14, wherein the hinge regions are circumferentially offset and the sigmoidal links attach on sides of the hinge regions.

18. A radially expansible luminal prosthesis as in claim 14, wherein the ring segments are expansible in response to a radially outward force; wherein at least one of the ring segments opens at a different rate or in a different amount than at least one other ring segment when exposed to the same radially outward force.

19. A radially expansible luminal prosthesis as in claim 18, wherein at least some struts in at least some of the serpentine rings have different lengths to cause the different rate of expansion.

20. A radially expansible luminal prosthesis as in claim 19, wherein at least some struts which are positioned away from the sigmoidal links are longer.

21. A radially expansible luminal prosthesis as in claim 18, wherein at least some of the struts have different widths than others of the struts to cause a different rate or amount of expansion.

22. A radially expansible luminal prosthesis as in claim 18, wherein at least some of the hinge regions have different widths than others of the hinges regions to cause a different rate or amount of expansion.

23. A radially expansible luminal prosthesis as in claim 14, wherein at least some of the struts are straight over the distance between the hinges.

24. A radially expansible luminal prosthesis as in claim 14, wherein at least some of the struts are non-linear.

25. A radially expansible luminal prosthesis as in claim 14, wherein the sigmoidal links are individually axially expansible and contractable.

26. A radially expansible luminal prosthesis as in claim 14, wherein the sigmoidal link is adapted to permit the connecting legs to move circumferentially past each other to accommodate radial crimping of the prosthesis.

* * * * *